(12) United States Patent
Makunga et al.

(10) Patent No.: US 10,188,689 B2
(45) Date of Patent: Jan. 29, 2019

(54) METHOD AND COMPOSITION FOR TREATING BREAST CANCER

(71) Applicant: STELLENBOSCH UNIVERSITY, Western Cape Province (ZA)

(72) Inventors: Nokwanda Pearl Makunga, Stellenbosch (ZA); Anna-Mart Engelbrecht, Cape Town (ZA)

(73) Assignee: STELLENBOSCH UNIVERSITY, West Cape Providence (ZA)

( * ) Notice: Subject to any disclaimer, the term of this patent is extended or adjusted under 35 U.S.C. 154(b) by 0 days.

(21) Appl. No.: 15/514,248

(22) PCT Filed: Sep. 25, 2015

(86) PCT No.: PCT/IB2015/057392
§ 371 (c)(1),
(2) Date: Mar. 24, 2017

(87) PCT Pub. No.: WO2016/046802
PCT Pub. Date: Mar. 31, 2016

(65) Prior Publication Data
US 2017/0274034 A1  Sep. 28, 2017

(30) Foreign Application Priority Data
Sep. 25, 2014  (ZA) .................................. 2014/06975

(51) Int. Cl.
*A61K 36/77* (2006.01)
*A61K 9/00* (2006.01)
*A61K 39/00* (2006.01)

(52) U.S. Cl.
CPC ............ *A61K 36/77* (2013.01); *A61K 9/0053* (2013.01); *A61K 39/0011* (2013.01); *A61K 2039/585* (2013.01)

(58) Field of Classification Search
CPC .................................................... A61K 36/77
USPC ......................................................... 424/774
See application file for complete search history.

(56) References Cited

U.S. PATENT DOCUMENTS

2006/0111310 A1* 5/2006 Chan ...................... C07H 15/24
                                                        514/33
2010/0093935 A1* 4/2010 Van ....................... A61K 47/645
                                                        525/54.2

OTHER PUBLICATIONS

Cao et al "Antiproliferative Triterpenoid Saponins of Dodonaea viscosa fron the Madagascar dry Forest", J. Nat. Prod. Sep. 2009; 72(9); 1705-1707.*
International Search Report for PCT/IB2015/057392, dated Dec. 16, 2015, 3 pages.
Written Opinion of the ISA for PCT/IB2015/057392, dated Dec. 16, 2015, 5 pages.
Cao et al., "Antiproliferative triterpenoid saponins of Dadonaea viscosa from the Madagascar dry forest", Journal of Natural Products, May 1, 2012, pp. 1705-1707.
Wagner et al., "Biologically active saponins from Dodonaea viscosa", Phytochemistry, vol. 26, No. 3, Jan. 1, 1987, pp. 697-701.
Rautenbach et al., "Investigating the potential of a traditional medicinal plant as an adjuvant remedy in the treatment of breast cancer", South African Journal of Botany—Suid-Afrikaans Tydskrift Virplantkunde, vol. 98, May 1, 2015, pp. 197-198.
Mossa et al., "Induction of Apoptosis through S-Phase in Human Breast Cancer MDA-MB231 Cells by Ethanolic Extract of *Dodonaea viscose* L.—an Iraqi Medicine Plant", Journal of Basrah Researches, Jan. 1, 2015, Retrieved from URL:http://www.basra-science-journal.org/cont41A1/9.pdf.
Imamura et al., "Comparison of 2D- and 3D-culture models as drug-testing platforms in breast cancer", Oncology Reports, vol. 33, No. 4, Apr. 1, 2015, pp. 1837-1843.

* cited by examiner

*Primary Examiner* — Christopher R Tate
*Assistant Examiner* — Deborah A Davis
(74) *Attorney, Agent, or Firm* — Nixon & Vanderhye P.C.

(57) ABSTRACT

The invention disclosed herein relates to the use of an extract of *Dodonaea viscosa* in breast cancer therapy, either alone or in combination with other breast cancer therapies.

9 Claims, 7 Drawing Sheets

METHOD AND COMPOSITION FOR TREATING BREAST CANCER

This application is the U.S. national phase of International Application No. PCT/IB2015/057392 filed 25 Sep. 2015, which designated the U.S. and claims priority to ZA Patent Application No. 2014/06975 filed 25 Sep. 2014, the entire contents of each of which are hereby incorporated by reference.

CROSS-REFERENCE TO RELATED APPLICATIONS

This application claims priority to South African provisional patent application number 2014/06975 filed on 25 Sep. 2014, which is incorporated by reference herein.

FIELD OF THE INVENTION

A plant extract for use in breast cancer therapy is provided.

BACKGROUND TO THE INVENTION

Breast cancer is the most common cancer in woman worldwide, contributing more than 25% of the total number of new cases diagnosed in 2012 (Ferlay et al., 2013). In South Africa, incidence rates are predicted to reach six times current levels by 2050 and overall African mortality rates are among the highest in the world (Bateman, 2012).

The standard cancer therapies used today, however, drastically compromise the homeostasis of normal cells, thus limiting their clinical effectiveness (Gerl, 2005). The anthracycline, doxorubicin (Dox), is one of the most effective anti-neoplastic agents used in the treatment of breast cancer and various other cancers (Octavia et al, 2012), However, its clinical effectiveness is limited due to its side effects, which include cumulative and dose-dependent cardiac toxicity (Gharib and Burnett, 2001; Takemura and Fijuwara, 2007; Zhang et al., 2009). Furthermore, cancer cells are becoming increasingly resistant to conventional therapy.

There is therefore a need to develop new treatment strategies which have the ability to target breast cancer tumour cells without harming normal cells and which circumvent the chemo-resistant phenotype.

SUMMARY OF THE INVENTION

According to a first embodiment of the invention, there is provided an extract of Dodonaea viscosa for use in breast cancer therapy.

The extract may be from the leaves or roots of the plant.

The plant extract may be obtained using water and/or an organic solvent, such as dichloromethane, hexane, petroleum ether, chloroform, hexane, acetone, methanol, ethanol, isopropanol, ethyl acetate, dimethyl sulphoxide, butanol, toluene, formic acid or acetonitrile. For example, the extract may be obtained using a water/acetonitrile/formic acid mixture as solvent, The extract may be a whole extract of the plant. Alternatively, the extraction process may be subjected to one or more separation steps so that compounds which are not active against breast tumour cells are excluded from the extract.

The extract may be used together with another anti-cancer agent, such as a pharmaceutical composition (e.g. chemotherapeutic agent). The extract may be an adjunct to the other anti-cancer agent. The extract and other anti-cancer agent may be administered separately or together.

The extract may be from any of *D. viscosa* L. Jacq., *D, viscosa* subsp. *angustifolia, D. viscosa* subs p.*angustissima, D. viscosa* subsp, *burtnenniene, D. viscosa* subsp. *cuneate, D. viscosa* subsp, *mucronate*, or *D. viscosa* subsp,*spatulata*. More preferably, the *D. viscosa* is *D. viscosa* L. Jacq., and even more preferably, the *D. viscosa* plant is from the Stellenbosch area.

According to a second embodiment of the invention, there is provided a composition for use in breast cancer therapy, the composition comprising an extract from *D. viscosa* as described above and one or more pharmaceutically acceptable excipients and/or adjuvants.

The composition may be in a formulation for oral administration, such as a capsule, tablet or liquid.

According to a third embodiment of the invention, there is provided the use of an extract as described above in a method of making a medicament for use in breast cancer therapy.

The medicament may include the extract and one or more pharmaceutically acceptable excipients and/or adjuvants.

According to a fourth embodiment of the invention, there is provided a method for preparing a plant extract having activity against breast tumour cells for use in breast cancer therapy, the method including the steps of:
  drying material of a *D. viscosa;*
  pulverising the dried material;
  mixing the pulverised material with a solvent to allow compounds from the material to leach into the solvent; and
  removing the pulverised material from the solvent, such that the plant extract remains in the solvent.

The material may be leaf or root material of *D. viscosa*.

The solvent may be selected from water and/or an organic solvent, such as dichloromethane, hexane, petroleum ether, chloroform, hexane, acetone, methanol, ethanol, isopropanol, ethyl acetate, dimethyl sulphoxide, butanol, toluene, formic acid or acetonitrile. For example, the extract may be obtained using a water/acetonitr ile/formic acid mixture as solvent.

The extract may be formulated into an oral dosage form, such as a capsule, tablet or liquid.

According to a fifth embodiment of the invention, there is provided a method of treating breast cancer, the method comprising administering to a subject in need thereof a therapeutically effective amount of an extract or composition as described above.

The extract or composition may be orally administered to the subject.

The extract or composition may be administered with another anti-cancer agent, such as a chemotherapeutic or other pharmaceutical composition.

DETAILED DESCRIPTION OF THE INVENTION

*Dodoneea viscosa* is described herein for use in treating breast cancer, either on its own or in addition to other breast cancer therapies. For example, the extract may be used as an adjunct to a cancer therapy such as chemotherapeutic treatment.

Figure 1:
FIG. 1 shows photographs of *D. viscosa* collected from Stellenbosch (left), De Hoop (centre) and Cederberg (right). Photography by Mr Carlo Randall.

*Dodoneee viscosa* is one of the less studied plant species of the Western Cape, South Africa. It is classified within the Family Sapindaceae (Getie et al, 2003). There are seven sub-species recognised, i.e. *D. viscosa* subsp. *angustifolia*, *D. viscosa* subs p.*angustissima*, *D. viscosa* subsp. *burmanniana*, *D. viscosa* subsp. cuneate, *D. viscosa* subsp. rnucronata, *D. viscosa* subsp.*spatulata* and *D. viscosa* subsp. *Viscose* (*D. viscosa* L. Jacq). Major differences that exist between the sub-species are in form and leaf characteristics and geographical distribution (FIG. 1) (McDowell, 2009). The plant is an evergreen shrub commonly found on sandy soils in tropical and subtropical regions (Naidoo, 2012), In general *D. viscosa* contains saponins, di-and triterpenes, flavonoids and a complex mixture of other phenolic compounds. In light of this, it is probable that any therapeutic activity perceived in this herb is linked to polyvalent pharmacological effects resulting from the synergistic combination of numerous components and not by any single isolated one (Wagner, 2005).

Root extracts from *D. viscosa* L. Jacq. have been used in traditional medicines for treating various diseases. *D. viscosa* has been used by aboriginal Australians as a traditional remedy to treat toothache, cuts and stingray stings (McDowell, 2009). Recent studies of *D. viscosa* have also shown immuno-modulatory (Jagtap et al., 2011) and anti-proliferative activity against the A2780 human ovarian cancer cell line (Cao et al., 2009). More recently, Rashed et al. (2013) found that *D. viscosa* petroleum ether extract has potential anti-HIV-1 agent activity.

In this study, a metabolomic approach was used to assess differences in populations of *D. viscosa*, as the activity of herbal extracts is influenced by the environment. The effects of the plant extracts were characterized in a non-invasive estrogen receptor positive human cancer cell line (MCF-7), a metastatic estrogen receptor negative human cancer cell line (MDA-MB-231) and a normal breast epithelial cell line (MCF-12A), whereafter its anti-neoplastic effects were examined in vivo in a tumour-bearing mouse model.

The extract can be from any part of the plant, such as the leaves, roots, fruit or seeds. In one particular embodiment of the invention, the extract is from the leaves. An organic solvent andior water can be used to obtain the extract from the plant material. Suitable organic solvents include dichloromethane, hexane, petroleum ether, chloroform, hexane, acetone, methanol, ethanol, isopropanol, ethyl acetate, dimethyl sulphoxide, butanol, toluene, formic acid and acetonotrile.

The extract can be from any of the *D. viscosa* subspecies, i.e. *D. viscosa* L. Jacq., D. viscosa subsp. *angustifolia, D. viscosa* subsp.*angustissima, D. viscosa* subsp. burmanniana, *D. viscosa* subsp. cuneata, *D. viscosa* subsp. rnucronata, or *D. viscosa* subsp.*spatulate*. In a particular embodiment, the extract is from *D. viscosa* Jacq., and in a further embodiment the extract is from the Stellenbosch geographical region of South Africa (Cape Winelands Municipality).

The invention will now be described in more detail with reference to the following non-limiting examples.

EXAMPLES

Methods and Materials
Plant Material and Field Collections

For the cytotoxicity study, Dodoneey viscosa samples were collected on the 20th Apr. 2012 from the highest slopes of the Stellenbosch mountain (33° 93' 614"S, 18°, 86', 019"E) by members of the Cape Bush Doctors Association (CBD). The CBD is a non-profit organization of collective represent members that trade, administer and/or utilize plant medicines. They base their indigenous knowledge (I.K.) on Khoi-San practices (Philander, 2012).

For the metabolomic study, samples were collected from populations of *D. viscosa* at three different sites during April to May, 2013. The study was in collaboration with the Cape Bush Doctors Association and members of this community assisted with plant collections. In the first population, six samples were collected to test for intra-population variation: the samples were equally divided to be sampled at two different altitudes. A total of nine samples among the three populations were used to analyze inter-population variation. A permit (Permit no: 0028-AAA008-00095) to harvest endangered plants was obtained from Cape Nature far plant collection at Stellenbosch Mountain, Cederberg mountain catchment area and De Hoop Nature reserve.

Plant species were identified and deposited as voucher specimens to the Stellenbosch University herbarium. The samples were stored after drying at 40° C. and kept in the dark at the Department of Botany and Zoology (Stellenbosch University).

Extraction Procedures

Metabolomic Study of Population Chemotypes

In an initial screen, twenty grams plant was pulverized and extracted using three different solvents: methanol; water; a 49.5% water :49.5% acetonitrile :1% formic acid mix (W:A:F;v/v). Many of these solvents are widely used because of their ability to increase the extract yield and aqueous extractions are general practice of preparing traditional medicines. For each gram of plant material, 10 ml of solvent was added. Each extract was placed in a sonication bath for 45 minutes and these extracts were then filtered using Whatman No. 1 filter paper. The extraction process was repeated twice. These extracts were then dried in a Speedvac® until completely dry. The water extracts were freeze-dried for 24 hours. For the intra-and inter-population analyses, the same methodology as for the initial screening experiment was followed, but only one gram of plant material was pulverized per extract and WA:F used as the solvent.

In Vitro and In Vivo Cytotoxicity Study

The extraction procedure was the same as for the metabolomic study, but for the purpose of this study ethanol was used as the solvent. After extraction the samples were freeze-dried. Freeze drying yielded 3.35 g of extract, which was stored in a desiccator. The extract was dissolved in 100% ethanol and suspended in growth medium to give a stock concentration of 50 mg/mL (Naidoo, 2012; Pengelly, 2008:4). The concentration of ethanol in extract preparations was restricted to 1.7% to minimize potential effects of the solvent on the growth of cells.

Metabolite Profiling of Plant Extracts

The dried extracts were resuspended in 100% (v/v) methanol to give a stock concentration of 50 mg/mL (Naidoo, 2012; Pengelly, 2008:4) and then alternately vortexed for 1 minute and sonicated for ten minutes until completely resuspended.

These solvents were evaluated using Liquid Chromatography Mass Spectrometry (LC/MS) as a measure of determining effects of extraction with the different solvents, For the intra-population variation analysis, six samples from De Hoop were tested for individual variation in a close-proximity population. For the inter-population variation analysis, three samples were taken from each population, amounting to a total of nine samples tested for inter-population chemical variation, Chromatographic separations and determination was performed on a Waters Synapt G2 quadrupole time-of-flight mass spectroscopy (Milford, Mass. USA) equipped with Waters Acquity ultra-perfomance liquid chromatography (UPLC LG 50 nm), Acquity photo diode array (PDA) detector and an auto-sampler. Metabolites were separated using a gradient of $H_2O$ with 0.1% formic acid (solvent A) and acetonitrile (solvent B), using a Waters UPLC at a flow rate of 0.4 ml min$^{-1}$ on a Waters BEH C18, 2.1×100 mm column, Three repeats per sample were injected and each run took 15 minutes. Positive and negative modes were employed at a cone voltage of 15 V and capillary voltage of 2.5 kV for mass separation of analytes. MassLynx® 4.1 software was utilized for data analysis. Assessment of the inter-relationships between the metabolite profiles of individual plants was done using principal component analysis (PCA-X) and hierarchical cluster analysis (HCA).

Physiological Studies

Cell Lines

For the cytotoxicity study on the Stellenbosch population, MDA-MB-231, a human metastatic mammary carcinoma cell line (American Type Culture Collection, Rockville, USA) and MCF-12A, a human, non-tumorigenic breast epithelial cell line (University of Cape Town) were utilized. Cell lines were cultured at 37° C. and 5% $CO_2$ in sterile Dulbecco's Modified Eagle's Medium (DMEM) (Sigma-Aldrich, D5796), supplemented with 10% fetal bovine serum (Invitrogen Gibco, 10270-106) and 1% PenStrep (Invitrogen Gibco, 15140-122). Cells were aliquot to 50 mL falcon tubes. The MCF-12A cell line was further supplemented (on day of use) with 50% Nutrient Ham-F12 (Invitrogen Gibco, 21765-029), 500 ng/mL hydrocortisone (Sigma-Aldrich, H0888), 10 ug/mL insulin (pharmacy), 100 ng/mL cholera toxin (Sigma-Aldrich, C8052) and 20 ng/mL epidermal growth factor (EGF) (Invitrogen Gibco, 10450-013). Cell lines were initially grown in 5 ml growth medium in T75 flasks and upon reaching the desired confluency (70-80%), the cells were passaged by incubation with TrypLET™ Express (Invitrogen Gibco, 12604-013).

For the population chemotypes study MCF-7, a human breast adenocarcinoma cell line (American Type Culture Collection, Rockville, USA) and MCF-12A were utilized. These two cell lines were cultured in 24-well plates, following the same procedure as described above. Once the desired confluency (70-80%) was reached the cells were passaged by incubation with TrypsinEDTA™ (Life Technologies).

Splitting and Seeding of Cells

The cells were split when a confluency of ~80% was reached (viewed under 20× objective). Growth medium, trypLE express/TrypsinEDTA and PBS were warmed in the 37° C. water bath. Old medium was discarded and the cell monolayer rinsed once with PBS. PBS was then discarded and 4 ml trypLE express added and cells placed in the shaker incubator for ~4 min. For trypsin, cells were neutralised with double the amount of media. Once cells have loosened contents were transferred to a falcon tube and then centrifuge at 1500 rpm for 3 minutes. The supernatant was decanted, leaving just a pellet of cells. 4 ml warm medium was added to the pellet and gently resuspended (using a 1000 μl pipette). Resuspended cells were counted using a haemocytometer. After splitting and seeding, cells were left to adhere for 48 hours before changing the medium.

Treatment of Cell Lines

Once the desired confluency was reached, medium was refreshed. Extracts were dissolved in 100% EtOH and complete media to a final concentration of 50 mg/mL, The solution was vortexed and then centrifuged at 1500 rpm for 3 minutes where after the supernatant was transferred to a new tube and the pellet discarded. For the cytotoxicity study on the Stellenbosch population, cells were treated with different concentrations of the extract (2.1, 4.2, 8.3, 16.7, 25 and 41.6 mg/mL) and incubated for 24 hours at 37° C. In addition, 1 μM Doxorubicin (Dox) (Sigma-Aldrich, D1515) was added to the MCF-12A and MCF-7 cells and used as a comparative cancer therapy. A vehicle control containing ethanol was used to determine whether the solvent had any effects on cell growth and/or viability. The same procedure was followed for the metabolomics study of population chemotypes, but the cells were treated with a standard concentration of 2.1 mg/mL (EtOH at a final concentration of 0.7%).

MTT Cell Viability Assays—In Vivo and In Vitro Cytotoxicity Study

Cells were cultured in 96-well plates at a density of approximately $8×10^3$ cells for MCF-12A and $5×10^3$ cells for MDA-MB-231 cells and allowed to proliferate in 100 uL growth medium, Once confluent, the old medium was discarded, the cell monolayer rinsed with PBS, the medium refreshed where after treatment was initiated. Following treatment, the medium was discarded and 50 μl of MTT (Sigma-Aldrich, M2128) working solution (0.01 g MTT/500 μL PBS) and 150 μL. PBS added to each well and incubated for 1 hour at 37° C. After incubation, supernatants were carefully aspirated and 200 μl of Isopropanol-HCL/Triton-X-100 (50:1) solution added to each well. Samples were gently agitated for 5 minutes on a shaker in order to dissolve formazan crystals. Absorbance was determined at 540 nm using a microliter plate reader and cell viability expressed as the fraction of viable, treated cells relative to untreated (control) cells. For the metabolomics study on population chemotypes, four samples were chosen to run MTT assays to test cell viability of both the normal non-tumorigenic breast epithelial cell line (MCF-12A) and the breast cancer cell line (MCF-7) after treatment. The same protocol as described for the cytotoxicity study was followed, but the cells were cultured in 24-well plates at a density of approximately $5 \times 10^4$ cells for MCF-12A and $5 \times 10^4$ cells for MCF-7 and allowed to proliferate in 100 μL growth medium. 125 μl of MTT (Sigma-Aldrich, M2128) working solution (0.01 g MTT/500 μL PBS) and 375 μL PBS was then added to each well. Each experiment was repeated three times.

In Vivo Model

Eight week old female C57BL6 mice (Tygerberg breeding facility) weighing 16-21g were housed in groups of 6-8 in Ehret cages (Emmedingen, Germany) in the animal house of the Department of Physiology, Stellenbosch University. The environment was temperature and humidity controlled, with a 12 hour light/dark cycle. This part of the study was carried out according to the guidelines of Stellenbosch University for the care and use of laboratory animals, The mice were fed standard chow and could eat and drink ad libitum. Mice were randomly divided into (i) control, (ii) Dox and (iii) plant extract groups and initial weights were recorded.

Tumour Establishment

A murine, metastatic mammary adenocarcinoma cell line (E0771) was received as a gift from Fengzhi Li (Roswell Park Cancer Institute, New York, USA). These cells were maintained in the same mariner as the MDA-MB-231 cells. Once 70% confluent, $2.5 \times 10^5$ cells in a volume of 200 μL were injected subcutaneously into the lower abdomen, close to or in the fourth mammary fat pad of each mouse (protocol adapted from Ewens et al. 2006), using a 23-guage needle. Tumours were evident after a period of three weeks, at which point the tumour size was measured.

Mouse Treatment

Following the weighing and grouping of mice, treatment with *D. viscosa* extract commenced. Tumour size was measured every two days by taking measurements in two perpendicular dimensions using digital calipers. The *D. viscosa* extract was administered through raspberry flavoured jelly blocks. Mice were conditioned to the taste of the jelly four days before treatment began. Human dosage (5.24 mg/kg/day) and the $K_m$ factor were used for dose translation based on body surface area to calculate animal dosage to be administered (Reagan-Shaw et al., 2007). On the day of treatment, mice were put in separate cages and given a 1 cm×1 cm block of jelly injected with 146 μL extract per jelly block (0.065 mg/g average bodyweight) at dusk every day, for a period of seven days. The day after the last treatment, mice were sacrificed by decapitation, where after tumours were harvested and frozen at −80° C. until needed.

Western Blot Analysis

Protein extraction from cells took place after the 24 hour treatment period. The medium was aspirated and the flasks were placed on ice. Cell monolayers were washed three times with ice cold PBS. Whole cell protein was extracted by incubating the cells for ±10 minutes in 300 μl of modified radioimmunoprecipitation (RIPA) buffer (pH 7.4), (in a T25) containina: Tris-HCL 2.5 mM, EDTA 1 mM, NaF 50 mM, NaPPi 50 mM, dithiothreitol 1 mM, phenylmethylsulfonyl fluoride (PMSF) 0.1 mM, benzamidine 1 mM, 4 mg/ml SBTI, 10 mg/ml leupeptin, 1% NP40, 0.1% SDS and 0.5% Na deoxycholate. The cell monolayer was scraped using a sterile, rubber policeman and transfer to chilled eppendorf tubes. Whole cell lysates were sonicated using an Ultrasonic Liquid Processor. Cell lysates were then centrifuged at room temperature for 10 minutes at 8000 rpm, where after the protein content of each lysate was determined using the Bradford method (Bradford, 1976). Protein samples were prepared and stored at −80° C. until needed. Protein was extracted from tumours by cutting a small piece from each tumour and placing it into a test tube with 1 mL RIPA and 5 μL PMSF. Samples were then homogenized and put on ice for foam to settle, then spun down at 8000 rpm for 10 minutes where after the supernatant was placed into a clean eppendorf tube. After extraction protein content was determined with the Bradford method (Bradford, 1976) and stored at −80° C. until analysis, Prepared samples were thawed and then boiled at 95° C. for 5 minutes before being centrifuged for a few seconds, 20 μg of protein was loaded into the wells of 4 -15% Tris-Glycine precast gels (Bio-Rad, 4561085) and separated by sodium dodecyl sulphate polyacrylamide gel electrophoresis (SDS-PAGE) for 25 minutes, at 250 V, 400 mA. A BLUeye Prestained Protein Ladder (GeneDirex, PM007-0500) was loaded into the first well of each gel in order to determine the molecular weights of specific bands and to orientate the gel. Proteins were transferred onto PVDF (polyvinylidene fluoride) membranes (Trans-Blot® Turbo™ Mini PVDF Transfer Packs, Bio-Rad, 170-4156) using the TransBlot® Turbo™ Transfer System (Bio-Rad) for 12 minutes at 15 V, 2.5 A. PDVF membranes were then blocked in 5% fat-free milk powder dissolved in 100 mL Tris Buffered Saline-Tween Solution (TBS-T) (5 g/100 ml TBS-T) at room temperature for one hour. After blocking, membranes were rinsed 3 times with TBS-T and incubated overnight at 4° C. with the respective primary antibodies (Cell Signalling Technology) in TBS-T. The primary antibodies used were p53, phospho-p53 Serf 5, cleaved caspase-3, cleaved PARP and PARP (diluted 1:1000), Subsequent to primary antibody incubation, membranes were washed 3 times with TBS-T and incubated with HRP-linked anti-rabbit secondary antibody (Cell Signalling Technology, #7074) for 1 hour at room temperature (diluted 1:4000). Membranes were washed with TBS-3 times and covered with Pierce ECL western blotting substrate (Thermo Scientific, #32106). Bands were detected using the ChemiDoc™ XRS+Sytem with the Image Lab™ Software (Bio-Rad), The bands generated were expressed as volume and represented as a percentage of the control sample (untreated). β-actin was used as a loading.

Statistical Analysis

Three different extracts per sample were done and profiled using LC/MS. Multivariate statistics was used for analysis of all metabolomic results obtained after LC/MS-profiling. PCA was applied to identify characteristic components with an important influence on the separation of the different groups. The methodology thus not only differentiated efficiently among samples, but the identification of characteristic components provided new valid chemical markers that have been proposed to be used for discrimination and quality control of *D. viscosa* samples. Hierarchical cluster analysis (HCA) was also applied to reduce the complex data sets into a series of optimized and interpretable views. HCA provides an insightful way at looking at large data sets for ease of interpretation. These views emphasize the natural groupings in the data and show which variables most strongly influence those patterns, thus allowing the identification of the likely principal component of the formula for this effect. The HCA was therefore in essence used to sort samples into groups by measuring similarity between samples. The similarity and dissimilarity between samples is represented in dendrogram for ease interpretation.

For the MTT assay testing cell viability, three repeats were done to test for repeatability. GraphPad Prism®, Version 5 for Windows®(GraphPad Software, San Diego, Calif.) was utilized for visual representation and statistical analysis of the data. One-way ANOVA was performed followed by Bonferroni post-hoc correction test. All values are expressed as a percentage of the control and the data is presented as the mean±standard error of the mean, A p-value of <0.05 was considered statically significant.

Results and Discussion

Metabolite Profiling of Different Populations

Figure 4:
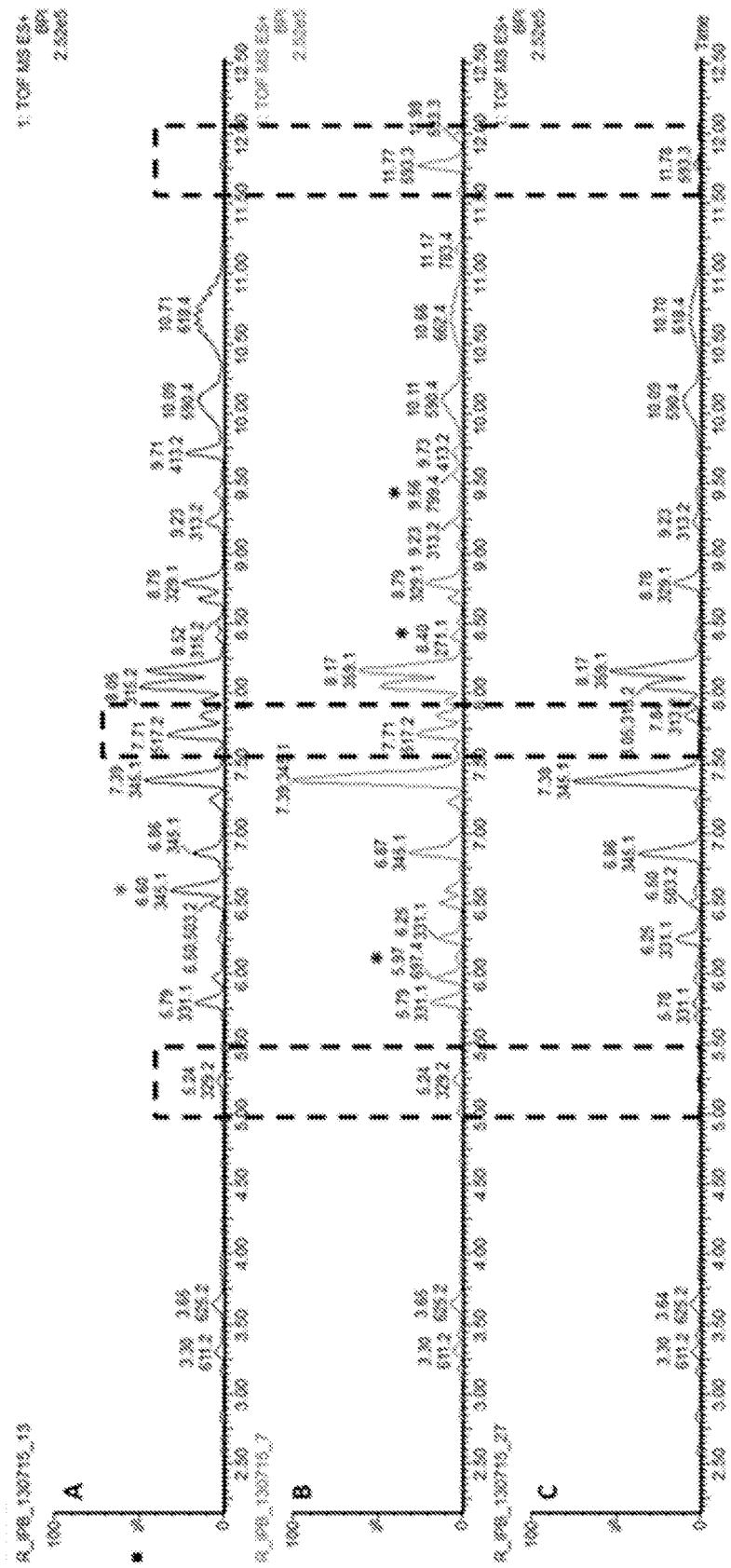
FIG. 4 shows chromatograms for samples from De Hoop (A), Cederberg (B) and Stellenbosch (C), illustrating differences in metabolite profiles that lead to clusters forming.

Similar metabolite profiles were obtained with the W:A:F and methanol extracts (FIG. 4). For further experimentation, the W:A:F was used as methanol may lead to chemical esterification during drying and storage. Aqueous extracts were not tested for further pharmacological action as water extracted fewer chemicals in comparison to the other solvents. Also, alcoholic tinctures are popular in the phytopharmaceuticals industry. Samples from De Hoop (FIG. 2A) differentiated based on altitude using the HCA. A clustering of samples from Stellenbosch and Cederberg indicated chemical similarities whilst samples from De Hoop formed a group of its own. Intra-population differences were evident for the De Hoop samples suggesting that both competition and altitude (having differences in temperature and wind, for example) may affect secondary metabolism. There are a few studies that illustrate chemically based acclimation among tropical plants along ecological gradients related to altitude (Goldstein et al., 1985; Ziska et al., 1992; Rada et al., 1998; Cabrera et al., 1998). Alonso-Amelot et al. (2004) indicated that synthesis of low molecular weight phenolics in neotropical *Pteridium* spp (brackens) in relation to altitude is probably a combined response to biotic and acclimation pressures. Plant natural products have a crucial function, especially when interacting with their biotic environment. They attract pollinators or seed dispersers, defend the plant against natural enemies or function as allelo-chemicals against competitors (Kroymann, 2011).

Figure 2:
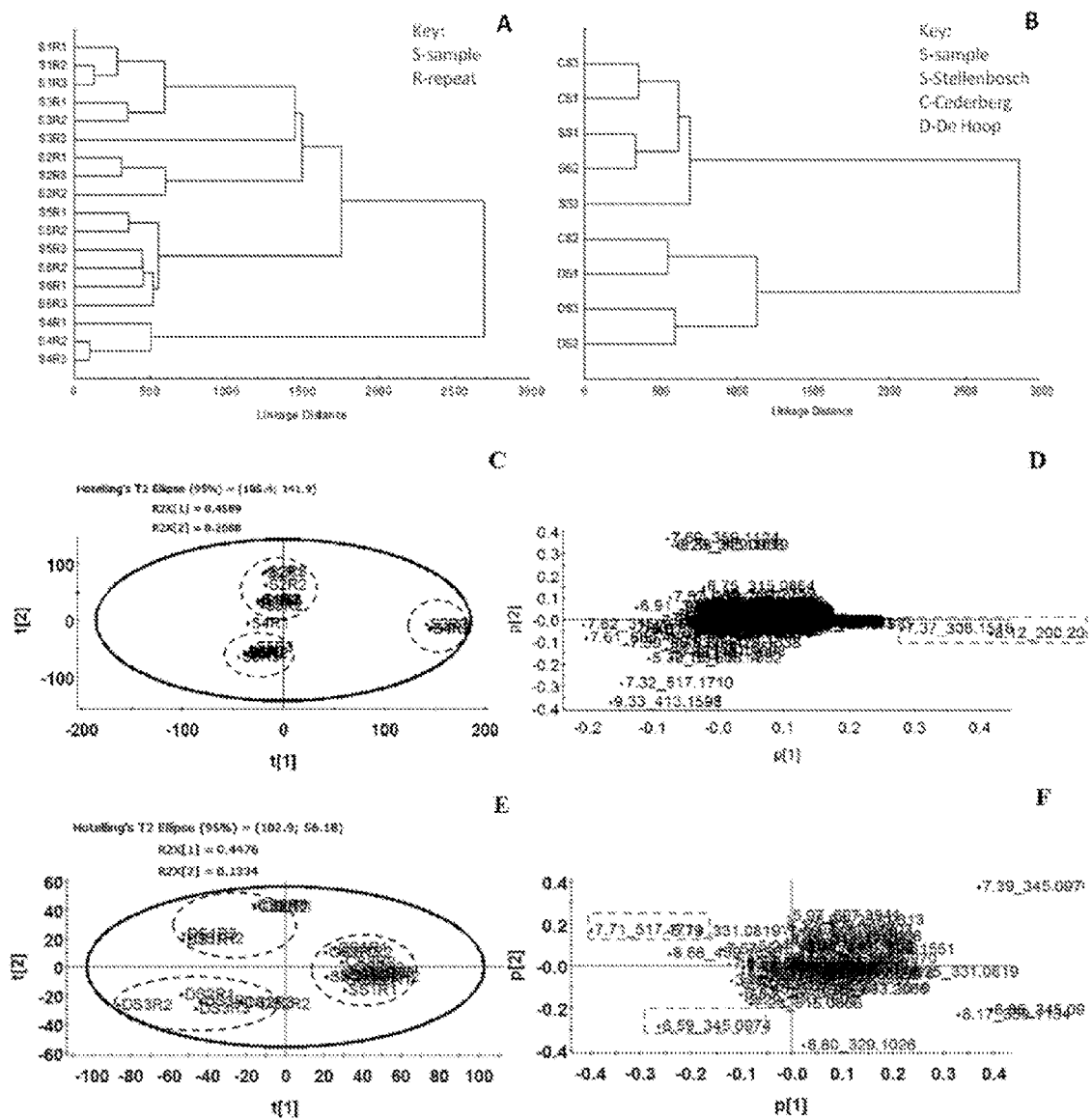
FIG. 2 shows hierarchical clustering of the intra-population chemical variation of samples collected in De Hoop (A) and the inter-population chemical variation of samples from De Hoop, Stellenbosch and Cederberg (B). PCA score (C) and loadings plots (D) for data from the intra-population study in De Hoop for samples 1-6, PCA score (E) and loadings (F) plots for data from the inter-population study among populations from De Hoop, Cederberg and Stellenbosch. D=De Hoop; S=Stellenbosch; C=Cederberg; S=sample; R=repeat.
Figure 3:
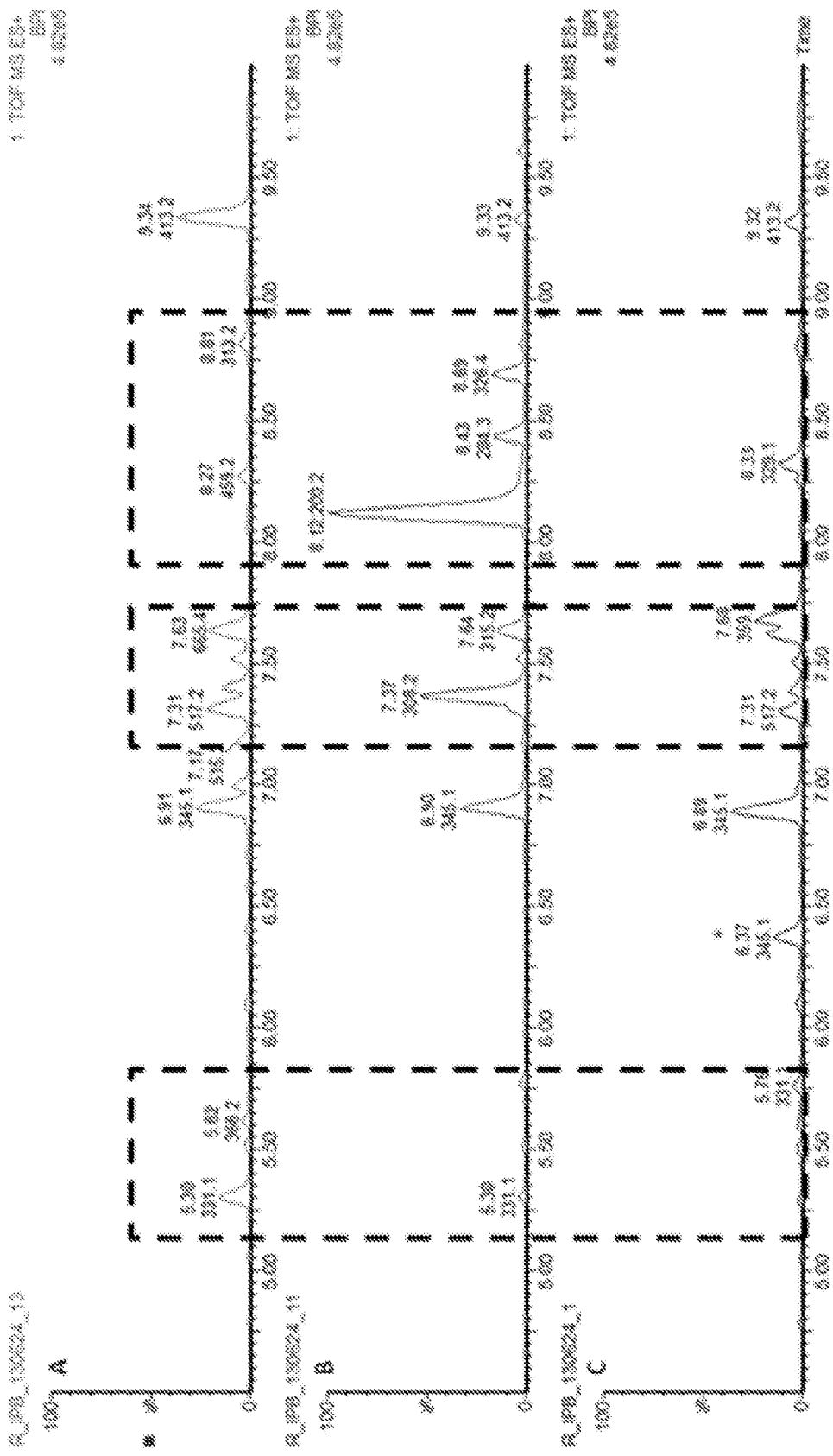
FIG. 3 shows chromatograms for samples 5 (A), 4 (B) and 1 (C) from De Hoop, illustrating differences in metabolite profiles that lead to clusters forming.

The PCA model consisted of 5 components. The plots explained 86% of the variance in the intra-population analysis ($R^2$(PC1)=0.4589; $R^2$(PC2)=0.2688 (FIG. 2C) and 65% in the inter-population analysis ($R^2$ (PC1)=0.4476; $R^2$ (PC2)=0.1334 (FIG. 2E). Three clusters were formed for samples from De Hoop. S3 and S4 from De Hoop had discriminating peaks at retention times 7.37 and 8.12 with molecular masses of 308.1518 and 200.20 respectively (FIGS. 2D and 3). In the inter-population study, DS3R2 and DS1 showed differentiation at retention times 6.59 and 7.71 with molecular masses of 345.09 and 517.17 respectively (FIGS. 2F and 4).

The Cederberg, situated in the Nama Karoo, displays a typical Mediterranean climate in the central region (mild, wet winters and warm summers), with more arid western and eastern regions. Rainfall ranges from 100 mm per annum along the coast, rising to 400 mm in the western mountains to over 700 mm on the highest mountains in the central (Low et al., 2004:8). There is a high range of climatic conditions due to the variation in topography. In winter the minimum temperature range is −3 to 3° C. with heavy frost sometimes occurring on high mountains, while in summer temperatures can increase to 39-44° C. Stellenbosch has a Mediterranean climate, with the most recent annual rainfall at 993.9 mm (La Colline Observatory, Stellenbosch Weather Station, 2014). Winters are cold and wet and during July temperatures can drop to 3.02° C. with snow falling on the surrounding mountains. Summer is warm and dry, with the temperature on some days rising to approximately 40° C. (Meijers, J. P., 2014). The Stellenbosch site is also prone to human disturbance. De Hoop Nature Reserve is not far offshore. It has a temperate Mediterranean climate, with warm summers and mild winters with a minimum temperature of approximately 6° C. in July and a maximum of 27° C. during January-February. The annual rainfall is about 564 mm with the highest rainfall usually during April/August (European Union, 2010a). These differences in environmental conditions are important.

Secondary metabolism by nature has very high genetic plasticity and diversity that makes the flexible adaptations of plants possible to the difficulties of a dynamic environment. A unique set of secondary compounds that are well adapted to the specific strains of the plant's ecological niche are found in each plant population (Hartmann, 2007). Cederberg and Stellenbosch have colder and wetter winters in comparison to De Hoop, and these two sites are situated more inland. These ecological differences may explain the differences in the chemical signatures which lead to separation of the De Hoop cluster on the negative vector of principle component 1 (PC 1) (FIG. 2E). Compounds of interest at the discriminatory peaks were analysed and compared to reported MS data (Yagudaev et al., 1968; Shakirov and Avazmukhamedov, 1969; Sultanov et al., 1969) and MassBank database (Horai et al., 2010) (Table 1).

MTT Cell Viability Assay In Vivo and In Vitro Cytotoxicity Study

Figure 5:
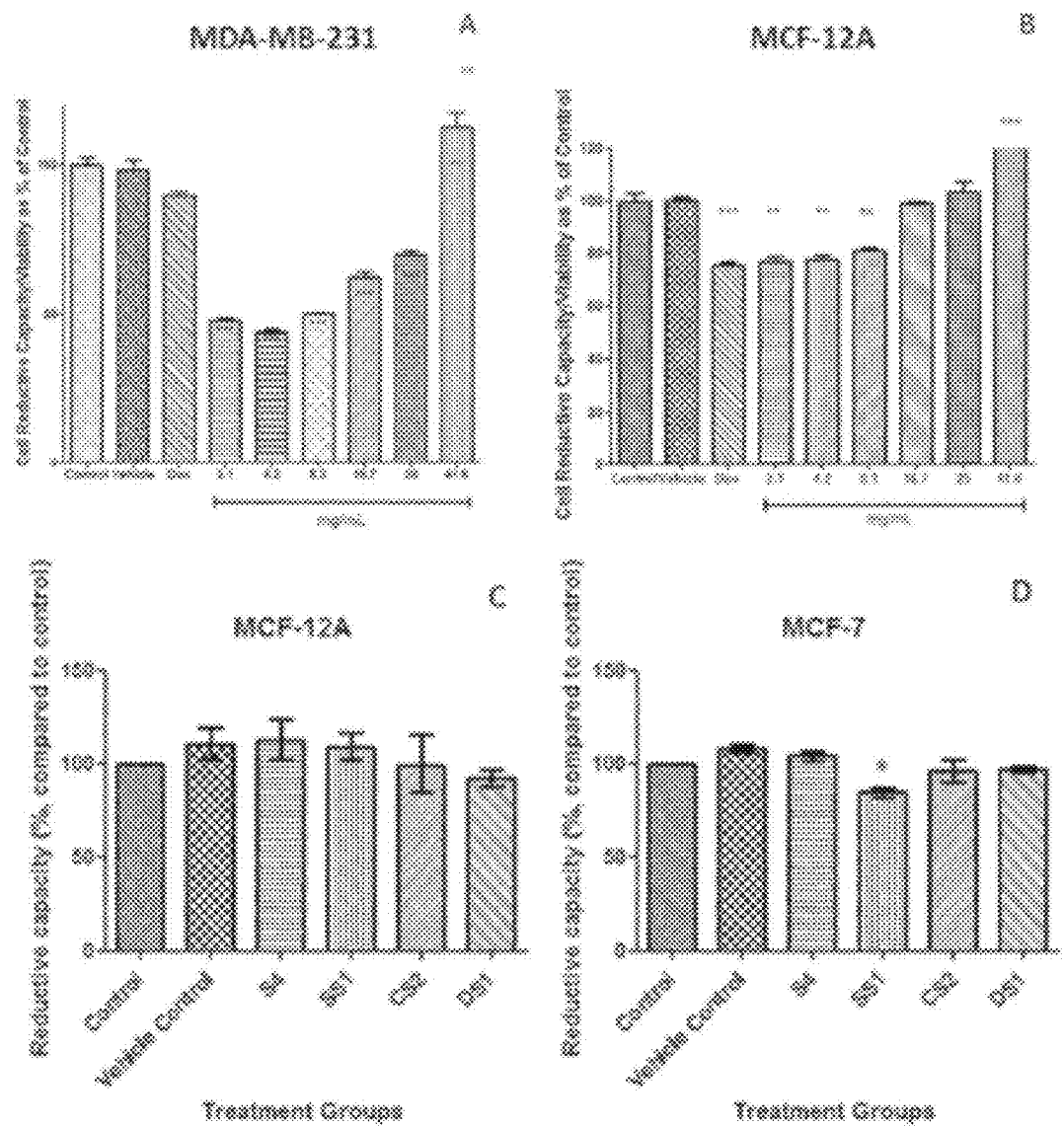
FIG. 5 shows MIT assays from the cytotoxicity study in Stellenbosch showing the effect of different concentrations (2.1, 4.2, 8.3, 16.7, 25 and 41.6 mg/mL) of a viscosa extract and Dox (1 µM), on the MTT reductive capacity of MDA-MB-231 cells (A) and MCF-12A cells (B) after treatment with the following concentrations 2.1, 4.2, 8.3, 16.7, 25 and 41.6 mg/mL of extract and Dox (1 µM) for 24 hours. MIT assays from the metabolomics study showing the effect of 2.1 mg/mL of $D.$ $viscosa$ extracts taken from different populations on the MTT reductive capacity of MCF-12A cells (C) and MCF-7 cells (D). DMEM was used as a control and ethanol was used as a vehicle control. All values are expressed as mean±SEM (n=3), *p<0.05, **p<0.01, p<0.001 versus the control, Dox=Doxorubicin; S4=Sample 4 from De Hoop; SS1=Sample 1 from Stellenbosch; CS2=Sample 2 from Cederberg; DS1=Sample 1 from De Hoop.

The effect of an alcoholic extract of *D. viscosa* from Stellenbosch on the viability of MDA-MB-231 cells was studied using the MTT assay following treatment with varying doses (FIG. 5A), After treatment over a 24-hour period, all concentrations, with exception to the 41.6 mg/mL were effective in reducing viability in the MDA-MB-231 cell line in comparison to Dox (47.88±0.83%, 44.33±0.73%, 50.10±0.39%, 62.30±1.94% and 70.04±0.87, p<0.001) and the control (100%). Unexpectedly, at the highest dose of 41.6 mg/mL, the extract appeared to induce cell proliferation (112.7±4.74%, p<0.01). The commercially used Dox also decreased cell viability (89.77±1.23%, p<0.01) compared to the control but was not as effective as the *D. viscosa* extract at concentrations of 2.1 to 25 mg/mL. The results showed (FIG. 5B) that the extract had similar effects on the growth of the MCF-12A cells when applied at 2.1 to 8.3 (p<0.01), Treatment with Dox resulted in a greater reduction in cell viability (75.58±1.26%, p<0.001) compared to both the control and all doses of the extract. In comparison to Dox, *D. viscosa* was significantly more cytotoxic to the breast cancer cells but less cytotoxic to normal cells, which therefore suggests that a concentration of 2,1 to 4.2 mg/mL of *D. viscosa* extract has the best potency against breast cancer cells, while causing little harm to non-cancerous cells.

TABLE 1

Retention times and ion fragmentation of tentatively identified compounds of interest using MS/MS methods

| RT | m/z | Ion fragments (+) | Compound | Elemental composition | Samples |
|---|---|---|---|---|---|
| 6.59 | 345.1 | 345.1, 287, 269, 244, 121 | Not identified | C18H16O7 | All samples from De Hoop |
| 7.37 | 308.1 | 308.1 | Foliosidine (BML00005) | C16H21NO5 | De Hoop sample 4 |
| 7.71 | 517.2 | 517, 473.1, 413.1, 357 | Not identified | C19H30l6 | All samples from De hoop, Cederberg sample 2 |
| 8.12 | 200.20 | 200 | Not identified | C12H26NO | De Hoop sample 4 |

MTT Cell Viability Assay Metabolomic Study of Population Chemotypes

For the MCF-12A cell line (FIG. 5C), none of the samples significantly reduced cell viability after treatment over a 24 hour period (114±4.67%, 110±3.01%, 101±6.33% and 92.7±2.02%, p>0.05), A significant difference in the reductive capacity between sample 1 and sample 4 from De Hoop for both the MCF-12A and MCF-7 cell lines (Bonferroni's Multiple Comparison Test). These differences corroborate the grouping of sample 4 and sample 1 from De Hoop as separate clusters. Differences in the chemical make-up were thus correlated to in vitro pharmacological activity. Out of the samples tested, the Stellenbosch extract produced the most significant reduction frequency (FIG. 5D) in the growth of the MCF-7 cell line (84.9±2.35%, p<0.05). Several studies have shown the importance of investigating herbal remedies for cytotoxic actions against cancer. For example, a bitter melon extract was reported to be effective against MDA-MB-231 (Ray et al., 2010). Leaf extracts of *Withania somnifera* also showed selective cytotoxicity to cancer cells (Widodo et al., 2007). At lower concentrations, extracts of *D. viscosa* was highly effective in the MDA-MD-231 cell line with little toxicity in the normal MCF-12 breast epithelial cell line (FIG. 5A and 5B). *D. viscosa* has been shown to be effective against cancer (Cao et al., 2009) but this is the first time this activity has been shown using a breast cancer cell line. Action on different cancers may be species-dependent due to the nature of the disease and/or chemicals which demonstrate cancer inhibition within a plant extract. The polyphenolic compounds found in many plants including *D. viscosa* are well known to have anti-oxidant properties as a result of their free radical scavenging activities (Fiorentino et al., 2007; Pietta, 1999; Wang et al, 2004). As in many other plants (Saleem et al., 2002), flavonoids, a type of polyphenol, are one of the most abundant compounds in *D. viscosa* (Cao et al., 2009; Venkatesh, 2008). However, these flavonoids also demonstrated pro-oxidant induced toxicity and apoptosis in HL-60 promyelocytic leukemia cells (Sergediene et al, 1999; Saleem et al., 2002).

Flavonoids auto-oxidize in aqueous media and can form highly reactive radicals. A study by Hirano et al. (1995) found that a citrus flavonoid induced apoptosis in HL-60 cells and Wei et al. (1994) confirmed that flavonoids caused the morphological changes in cells associated with apoptosis, in several cell lines. The anti-proliferative effects or the apoptosis induced by flavonoids on several cancer cell lines has been linked to phosphatidylinositol 3-kinase (PI3K) inhibition, cell cycle arrest and accumulation of p53 (Sergediene et al, 1999). Apoptosis is negatively regulated by PI3K and Akt signalling. These pathways readily engage several survival factors (Kasibhatla, 2003), therefore, the inhibition of PI3K/Akt will induce apoptosis. Oxidative damage plays an important role in aging and several degenerative diseases such as heart disease and cancer (Pietta, 1999; Fiorentino et al., 2007).

In Vivo Model

Figure 6:
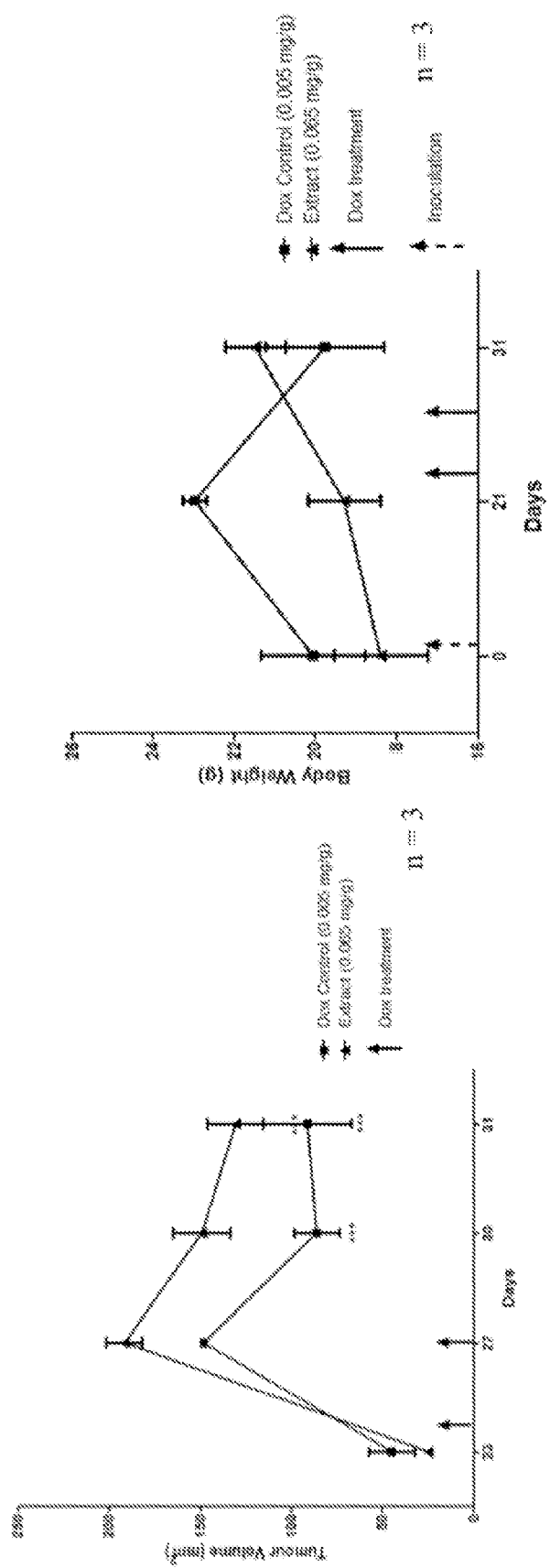
FIG. 6 shows the effect of Dox and a viscosa treatment on tumour volume (A) over a period of 7 days and the weight of mice (B) following inoculation and treatment. Values are expressed as mean±SEM (n=3), p<0.05.

Treatment with an alcoholic extract (0.065 mg/g average bodyweight) of *D. viscosa* and Dox (5 mg/g average body weight) reduced tumour volume over a 7-day treatment period, whilst the tumours in the control mice continued to grow (FIG. 6A). The average tumour volumes at the end of the study for the control, Dox and extract groups were 370, 106.51 and 130.94 mm$^2$, respectively. A study by Widodo et al. (2007) reported similar findings in their in vivo model; although malignant human fibrosarcoma cells were used, extracts of *Withania somnifera* resulted in tumour suppression, Although Dox and *D. viscosa* treatment were able to reduce tumour volume to more or less the same extent, it is interesting to note that the mice treated with the extract continuously gained weight during the course of the treatment, emphasizing the low toxicity of *D. viscosa* (FIG. 6B). *D. viscosa* has many chemicals which may be acting synergistically in promoting bio-activity and weight-gain and/or maintenance. As a whole extract, a variety of amino acids, carbohydrates and some lipophilic biochemicals may play a health-benefiting role. This may be important for use of the herbal remedy as an immuno-modulatory agent (Jagtap et al., 2011) which also benefits tumour reduction.

Western Blot Analysis of MDA-MB-231 Cells and Tumours in C57BL6 Mice

Figure 7:
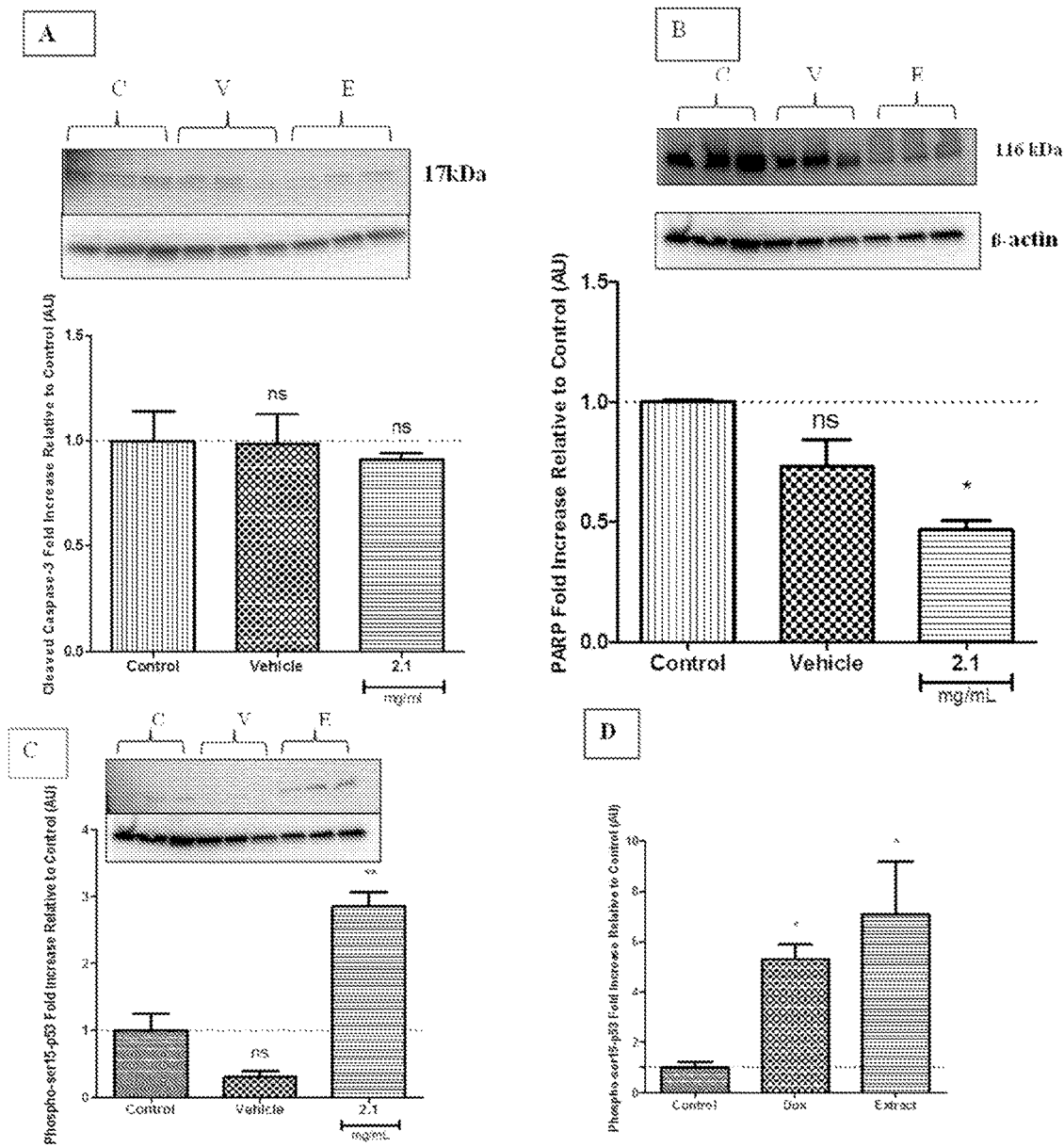
FIG. 7 shows In vitro Western blot analysis of the relative quantification of cleaved Caspase-3(A), cleaved PARP (B), Phospho-p53 (C) in MDA-MB-231 cells. Phospho-ser15-p53 (D) (presented as a ratio of phospho-ser15-p53 to total p53) following treatment of mice with Dox or $D.$ $viscosa$ for a period of seven days. Values are expressed as fold increase relative to control (n=3). ns—not significant (p0.05), *p<0.05 vs control.

The 2.1 mg/mL dose was selected as the desired concentration based on its ability to induce cell death in MDA-MB-231 cells (FIG. 6), To assess the impact of this concentration on cell death, apoptosis was investigated. *D. viscosa* (2.1 mg/mL) significantly induced PARP cleavage (FIG. 6B) in the MDA-MB-231 cells. There was also an increase in PARP cleavage in the tumours obtained from the mice to the same extent as what Dox induces, although it was not significant due to small n values, Interestingly, no significant differences were detected in cleaved caspase in the MDA-MB-231 cells nor in the tumours obtained from the mice (FIG. 7A). This might be attributed to the time of tissue collection, since caspase-3 cleavage precedes PARP cleavage; it might be that this event was already completed and removed via ubiquitin degradation (Suzuki, 2001) at the time the cells and tissue were collected.

On the other hand, Chan et al. (2011) reported the induction of apoptosis in breast carcinomas through caspase activity, following treatment with R. rohituka. Similarly, Ray et al. (2010) detected activated caspase-3 in MDA-MB-231 cells and MCF-7 cells following treatment with bitter melon extract. These data suggest that following 24 hours of treatment; caspase-3 was cleaved and activated, hence promoting apoptosis in MDA-MB-231 cells. Results from both the in vitro and in vivo experiments indicate that *D. viscosa* trigger the apoptotic pathway, resulting in PARP cleavage, PARP is cleaved early during apoptosis, by caspase-3, in order to prevent ATP depletion (Boulares et al., 1999), Following treatment with plant extract, phosphorylation of p53 Seri 5 was significantly increased (2.85±0.22, $p<0.01$) in all cells treated with 2.1 mg/mL of the plant extract (FIG. 7D). Expression of p53 is negatively regulated by its association with Mdm-2, an E3 ubiquitin ligase that promotes rapid degradation of p53 (Kasibhatla, 2003). Many agents have already been developed that are able to bind to Mdm-2, displacing and activating p53. The levels of total p53 may be low due to the short half-life of p53, whereas the phosphorylated p53 (serine 15) is significantly more expressed. Studies have shown that phospho-ser 15-p53 translocates into the mitochondria where it physically interacts with and inhibits Bcl-2, therefore promoting apoptosis (Park, 2005). At this stage, the exact mechanism of the *D. viscosa* extract requires intensive study. However, these data together allude to action via the phosphorylation of p53 at serine 15, and negative regulation linked to Mdm-2 activity for p53 activation.

Hui et al. (2006) has shown that MDA-MB-231 cells do not contain wild-type p53 but rather express mutant p53. The low levels of p53 expressed in the cells following treatment may be due to the fact that MDA-MB-231 cells express mutant p53 which interacts with and inactivates wild-type p53. Supporting this is the fact that although mutant p53 loses its apoptotic function, it remains capable of initiating cell cycle arrest, as seen by the low cell viability in the MTT assay (Lowe, 2000). Shin (2011) also observed p53 phosphorylation at Serine 15 following treatment of MCF-7 cells with an ethanol extract of *iris nertschinskia*. p53 induced apoptotic cell death as well as causing the over-expression of Bax and caspase cleavage. Following treatment with *D. viscosa* in C57BL6 mice, it is clear that the extract was able to induce apoptosis, as evident by PARP cleavage to the same extent as Dox induces (FIG. 7B). The tumours of the mice treated with the extract also showed significantly higher levels of phospho-p53 (7.093±2.964, $p<0.05$). The level of p53 in the Dox treated group was also significantly elevated (5.3±1.016, $p<0.05$) relative to the control, however, Dox did not differ from the extract group, Conclusion

*D. viscosa* has proven to be cytotoxic to breast cancer cells, but has shown limited toxicity to normal breast epithelial cells. The extract is effective at inducing apoptosis, as evident by the apoptotic markers detecting in Western blot analysis, but it remains non-toxic in vivo, and results in similar inhibition of tumour growth compared with the Dox treatment group and prevented weight-loss in mice over the course of treatment, The Stellenbosch population had the best anti-cancer activity and were similar to those from Cederberg in their chemical profiie.This extract may prove a novel phyto-therapy as an adjunct remedy, on its own or with other commercial drugs to assist in reducing proliferation of tumours.

REFERENCES

1. Alonso-Amelot, M. E., Oliveros, A., Calcagno-Pisarelli, M. P., 2004. Phenolics and condensed tannins in relation to altitude in neotropical *Pteridium* spp. A field study in the Venezuelan Andes. Biochemical Systematics and Ecology 32, 969-981.
2. American Cancer Society, 2013. Cancer Facts & Figures 2013. http://www.cancer.org/acs/groups/content/©epidemiologysurveilanceldocuments/document/acspc-036845.pdf. Accessed Oct. 29, 2013.
3. Bateman, C., 2012. Pink—the colour of hope for uninsured women. South African Medicinal Journal 102, 902-903.
4. Boulares, A. H., Yakovlev, A. G., Ivanova, V., Stoica, B. A., Wang, G., Iyer, S. & Smulson, M., 1999. Role of Poly (ADP-ribose) Polymerase (PARP) Cleavage in Apoptosis. The Journal of Biological Chemistry 274, 22932-22940.
5. Bradford, M. M., 1976. A Rapid and Sensitive Method for the Quantitation of Microgram Quantities of Protein Utilizing the Principle of Protein-Dye Binding. Analytical Biochemistry 72, 248-254.
6. Briskin, D. P., 2000. Medicinal Plants and Phytochemistry, Linking Biochemistry and Physiology to Human Health. Plant physiology 124, 507-541.
7. Buchanan, B., Gruissem, W., Jones, R., 2000. Biochemistry & Molecular Biology of Plants. American Society of Plant Physiologists, Rockville, Md.
8. Cabrera, H. M., Rada, F., Cavieres, L., 1998. Effects of temperature on photosynthesis of two morphologically contrasting plant species along an altitudinal gradient in the tropical high Andes. Oecologia 114, 145-152.
9. Cao, S., Brodie, P., Callmander, M., Randrianaivo, R., Razafitsalarna, J., Rakotobe, E., Rasamison, V. E., TenDyke, K., Shen, Y., Suh, E. M., Kingston, D. G. I., 2009. Antiproliferative Triterpenoid Saponins of *Dodonaea viscosa* from the Madagascar Dry Forest. Journal of Natural Products 72, 1705-1707.
10. Cederberg Municipality: Water Services Development plan 2009/2010. http://www,cederbergmunicipality.co.za/Documents/2013031372227_item_240920V01.pdf. Accessed Mar. 14, 2014.
11. Chan, L. L., George, S., Ahmad, I., Gosangari, S. L., Abbasi, A., Cunningharnd, B. T. & Watkin, K. L., 2011. Cytotoxicity effects of *Amoora rohituka* and *chittagonga* on Breast and Pancreatic Cells. Evidence-Based Complementary and Alternative Medicine 2011.
12. European Union, 2010*a*. Overview of Cederberg. http://bioval.jrc.ec.europa.eu/APAAT/. Accessed Mar. 14, 2014.
13. European Union, 2010b. Overview of De Hoop, http://bioval.jrc.ec.europa.eu/APAAT/. Accessed Mar. 14, 2014.
14. Ewens, A., Luo, L. & Berleth, E., 2006. Doxorubicin plus Interleukin:-2 Chemoimmunotherapy against Breast Cancer in Mice. Cancer Research 66, 5419-5426.
15. Ferlay, J, Soerjomataram, I., Ervik, M., Dikshit, R., Eser, S., Mathers, C., Rebelo, M., Parkin, D. M., Forman, D., Bray, F., 2013. GLOBOCAN 2012 v1.0, Cancer Incidence and Mortality Worldwide: IARC CancerBase No. 11. Lyon, France: International Agency for Research on Cancer. http://globocan.iarc.fr. Accessed Jun. 9, 2013.
16. Fiorentino, A., D'Abrosca, B., Pacifico, S., Golino, A., Mastellone, C., Oriano, P. Monaco, P., 2007, Reactive Oxygen Species Scavenging Activity of Flavone Glycosides from *Melliotus neapolitana*. Molecules 12, 263-270.
17. Gautam, R., Saklani, A., Jachak, S. M., 2007. Indian medicinal plants as a source of antimycobacterial agents, Journal of Ethnopharmacology 110, 200-234.
18. Geri, R., Vaux, D. L., 2005. Apoptosis in the Development and Treatment of Cancer, Carcinogenesis 26, 263-270.

19. Getie, M, Gebre-Mariama, T., Rietz, R., Hahne, C., Huschkad, C., Schmidtkee, M., Abatef, A., Neubertb, R. H. H., 2003. Evaluation of the anti-microbial and anti-inflammatory activities of the medicinal plants *Dodonaea viscosa, Rumex nervosus* and *Rumex abyssinicus*. Fitoterapia 74, 139-143.
20. Gharib, M. I., Burnett, A. K., 2001. Chemotherapy-induced cardiotoxicity: current practice and prospects of prophylaxis. European Journal of Heart Failure 4, 235-242.
21. Goldstein, G., Rada, F., Azócar, A., 1985. Cold hardiness and supercooling along an altitudinal gradient in an Andean giant rosette species. Oecologia 68, 147-152.
22. Hartmann, T., 2007. From waste products to ecochemicais: Fifty years research of plant secondary metabolism. Phytochemistry 68, 2831-2846.
23. Hirano, T., Abe, K., Gotoh, M. & Oka, K., 1995. Citrus flavone Tangeretin inhibits leukaemic HL-60 cell growth partially through induction of apoptosis with less cytotoxicity on normal lymphocytes. British Journal of Cancer 72, 1380-1388.
24. Horai, H., Arita, M., Kanaya, S., Nihei, Y., Ikeda, T., Suwa, K., Ojima, Y., Tanaka, K., Tanaka, S., Aoshima, K., Oda, Y., Kakazu, Y., Kusano, M., Tohge, T., Matsuda, F., Sawada, Y., Hirai, M. Y., Nakanishi, H., Ikeda, K., Akimoto, N., Maoka, T., Takahashi, H. Ara, T., Sakurai, N., Suzuki, H., Shibata, D., Neumann, S., Iida, T., Tanaka, K., Funatsu, K., Matsuura, F., Soya, T., Taguchi, R., Saito, K. and Nishioka. T., 2010. MassBank: a public repository for sharing mass spectral data for life sciences. Journal of Mass Spectrometry 45, 703-714.
25. Hui, L., Zheng, Y., Yen. Y., Bargonetti, J. & Foster, D. A. 2006. Mutant p53 in MDA-MB-231 Breast Cancer Cells is stabilised by Elevated Phospholipase D Activity and Contributes to Survival Signals Generated by Phospholipase D. Oncogene 25, 7305-7310,
26. Jagtap, A., Vyawahare, N., Shinde, N., Kakade, S., Pujari, R., 2011. Immunomodulatory activity of ethanolic extract of *Dodonaea viscosa* L.F. Pharmacology online 1, 685-701.
27. Jeggo, P. A., 1998. DNA Repair: PARP—Another Guardian Angel? Current Biology 8, 49-51.
28. Kasibhatla, S. & Tsang, B., 2003. Why Target Apoptosis in Cancer Treatment? Molecular Cancer Therapeutics 2, 573-580.
29. Kim, Y. S., Maruvada, P., Milner, J. A., 2008, Metabolomics in biomarker discovery: future uses for cancer prevention. Future Oncology 4, 93-102.
30. Kroyrnann, J., 2011. Natural diversity and adaptation in plant secondary metabolism. Current Opinion in Plant Biology 14, 246-251.
31. La Conine Observatory, Stellenbosch Weather Station, 2014. http://weather.icao.co.za/index.php/Special_CurrentWeather. Accessed Mar. 13, 2014.
32. Low, A. B., Mustart, P., van Der Merwe, H., 2004, Greater Cederberg Biodiversity corridor: Provision of Biodiversity for Management. Coastec, Rondebosch
33. Lowe, S. W. & Lin, A. W., 2000. Apoptosis in Cancer. *Carcinogenesis* 21, 485-495.
34. Makunga, N. P., Philander, L. E., Smith, M., 2008. Current perspectives on an emerging formal natural products sector in South Africa. Journal of Ethnopharmacology 119, 365-375.
35. McDowell, M., 2009. *Dodonaea viscosa*, Australian National Botanical Gardens. http://www.anbg.gov.au/gnp/interns-2007/dodonaea-viscosa.html. Accessed Mar. 7, 2013.
36. Meijers, J. P., 2014. Stellenbosch Weather. http://weather.sun.ac.za/. Accessed Mar. 14, 2014.
37. Middleton, E., Kandaswami, C., Theoharides, T. C., 2000. The Effects of Plant Flavonoids on Mammalian Cells: Implications for Inflammation, Heart Disease and Cancer. Pharmacological Reviews 52, 673-751.
38. Naidoo, R., Patel, M., Gulube, Z., Fenyvesi, I., 2012. Inhibitory activity of *Dodonaea viscosa* var. *angustifolia* extract against *Streptococcus mutans* and its biofilm. Journal of Ethnopharmacology 144, 171-174.
39. O'Donovan, N., Crown, J., Stunell, H., 2003. Caspase 3 in Breast Cancer. Clinical Cancer Research 9, 738-742.
40. Octavia, Y., Tocchetti, C. G., Gabrielson, K. L., Janssens, S., 2012. Doxorubicin-induced cardiomyopathy: from molecular mechanisms to therapeutic strategies. Journal of Molecular and Cellular Cardiology 52, 1213-1225.
41. Park, B., 2005. Phospho-ser 15-p53 transiocates into mitochondria and interacts with bcl-2 and bcl-xL in eugenol-induced apoptosis. Apoptosis 10, 193-200.
42. Pengelly, A., 2008. Medicinal activity of *Dodonaea viscosa*: A preliminary study. Rural Industries Research and Development Corporation, Kingston.
43. Philander, L. E. A., 2012. Hunting Knowledge and Gathering Herbs: Rastafari Bush Doctors In the Western Cape, South Africa. Journal of Ethnopharmacology 32, 134-156.
44. Pietta, P. G., 1999. Flavonoids as Antioxidants. Journal of Natural Products 63, 1035-1042.
45. Rada, F., Azócar, A., González, J., Briceño, B., 1998. Leaf gas exchange in *Espeletia schultzii* Wedd, a giant caulescent rosette species, along an altitudinal gradient in the Venezuelan Andes. Acta Oecologica-International Journal of Ecology 19, 73-79.
46. Rashed, K., Luo, M. T., Zhang, L. T., Zheng, Y. T., 2013. *Dodonaea viscosa* (L.) extracts as anti human immunodeficiency virus type-1 (HIV-1) agents and phytoconstituents. Peak Journal of Medicinal Plant Research 1, 19-25.
47. Ray. R. B., Raychoudhuri, A., Steele, R., Nerurkar, P., 2010. Bitter Melon (*Momordica charantia*) Extract Inhibits Breast Cancer Cell Proliferation by Modulating Cell Cycle Regulatory Genes and Promotes Apoptosis. Cancer Research 70, 1925-1931.
48. Reagan-Shaw, S., Nihal, M., Ahmad, N., 2007. Dose translation from animal to human studies revisited. Federation of American Societies for Experimental Biology 22, 659-661.
49. Salaam, A., Husheem, M., Härkönen, P., Pihlaja, K., 2002. Inhibition of cancer cell growth by crude extract and the phenolics of *terminalia chebula* retz. fruit. Journal of Ethnopharmacology 81, 327-336.
50. Sergediene, E., Jönsson, K., Szymusiak, H., Tyrakowska, B., Rietjens, I. M. C. M., 1999. Prooxidant toxicity of polyphenolic antioxidants to HL-60 cells: description of quantitative structure-activity relationships. Federation of European Biochemical Societies Letters 462, 392-396.
51. Shakirov, T. T. Avazmukhamedov, L. T., 1969. Isolation of perforine and foliosidine. Chemistry of Natural Compounds 5, 385-386.
52. Sharma, H., Parihar, L., Parihar, P., 2011. Review on cancer and anticancerous properties of some medicinal plants. Journal of Medicinal Plants Research 5, 1818-1835.
53. Shin, J. S., 2011. An ethanol extract of iris nertschinskia induces p53-dependent apoptosis in the MCF7 human breast cancer cell line. International Journal of Molecular Medicine 27, 401-405.

54. Street, R. A., Stirk, W. A., Van Staden, J., 2008. South African traditional medicinal plant trade-Challenges in regulating quality, safety and efficacy. Journal of Ethnopharmacology 119, 705-710.
55. Sultanov, S. A., Yunusov, S. Yu., 1969. Alkaloids of *Haplophylium dubium* accompanying foliosidine. Chemistry of Natural Compounds 5, 114-115.
56. Suzuki, Y., Nakabayashi, Y., Takahashi, R., 2001. Ubiquitin-protein ligase activity of X-linked inhibitor of apoptosis protein promotes proteasomal degradation of caspase-3 and enhances its anti-apoptotic effect in fas-induced cell death. Proceedings of the National Academy of Sciences 98, 8662-8667.
57. Takemura, C., Fujiwara, H., 2007. Doxorubicin-Induced Cardiornyopathy: From the Cardiotoxic Mechanisms to Management. Progress in Cardiovascular Diseases 49, 330-352.
58. Venkatesh, S., Reddy, Y. S. R., Ramesh, M., Swamy, M. M., Mahadevan, N., Suresh, B., 2001. Pharmacognostical studies on *Dodonaea viscosa* leaves. African Journal of Pharmacy and Pharmacology 2; 83-88.
59. Wagner, H., 2005. In Handbook of Medicinal Plants (Ed, Yaniv, Z. B., U.) Haworth press, New York.
60. Wang, S., Konorev, E. A., Kotamraju, S., Joseph, J., Kalivendi, S., Kalyanaraman, B., 2004. Doxorubicin Induces Apoptosis in Normal and Tumor Cells via Distinctly Different Mechanisms. Journal of Biological Chemistry 279, 25535-25543.
61. Wei, Y., Zhao, X., Kariya, Y., Fukata, H., Teshigawara, K., Uchida, A. 1994., Induction of apoptosis by quercetin: Involvement of heat shock protein. Cancer Research 54, 4952-4957.
62. Widodo, N., 2007. Selective killing of cancer cells by leaf extract of ashwagandha: Identification of a tumor-inhibitory factor and the first molecular insights to its effect. Clinical Cancer Research 13; 2298-2306.
63. Yagudaev, M. R., Yunusov, S. Yu., 1968. NMR spectrum of foliosidine. Chemistry of Natural Compounds 4, 74-175.
64. Zhang, Y-W, Shi, J., Li., Wei, L., 2009. Cardiomyocyte death in doxorubicin-induced cardiotoxicity. Archivum Immunologiae et Therapiae Experimentalis 57, 435-445.
65. Ziska, L. H., Teramura, A. H., Sullivan, J. H., 1992. Physiological sensitivity of plants along an elevational gradient to UV-B radiation. American Journal of Botany 29, 863-871.

The invention claimed is:

1. A method of treating breast cancer, the method comprising administering to a subject in need thereof a therapeutically effective amount of a plant extract from leaves of *Dodonaea viscosa* or a composition containing the extract.

2. The method of claim 1, wherein the plant extract or composition is administered to the patient with an additional anti-cancer agent.

3. The method of claim 1, wherein the plant extract is a whole extract of the leaves of the *Dodonaea viscosa* plant.

4. The method of claim 1, wherein the plant extract is obtained after one or more separation steps to remove compounds from the leaves of *Dodonaea viscosa* which are not active against breast tumour cells.

5. The method of claim 1, wherein the plant extract is from subspecies *D. viscosa L. Jacq.*

6. The method of claim 1, wherein the plant extract or composition is in an oral dosage form.

7. The method of claim 6, wherein the oral dosage form is selected from the group consisting of a capsule, tablet, powder and liquid.

8. The method of claim 1, wherein the treatment is not cytotoxic to non-cancerous cells.

9. The method of claim 3, wherein the whole extract contains saponins, diterpenes, triterpenes, and flavonoids.

* * * * *